United States Patent
Hettler et al.

(10) Patent No.: US 11,640,863 B2
(45) Date of Patent: May 2, 2023

(54) GLASS-METAL FEEDTHROUGH HAVING A SLEEVE

(71) Applicant: SCHOTT AG, Mainz (DE)

(72) Inventors: Robert Hettler, Kumhausen (DE); Wee Kiat Chai, Singapore (SG); Rainer Graf, Landshut (DE)

(73) Assignee: SCHOTT AG, Mainz (DE)

( * ) Notice: Subject to any disclaimer, the term of this patent is extended or adjusted under 35 U.S.C. 154(b) by 3 days.

(21) Appl. No.: 16/890,463

(22) Filed: Jun. 2, 2020

(65) Prior Publication Data
US 2020/0381147 A1    Dec. 3, 2020

(30) Foreign Application Priority Data

Jun. 3, 2019    (DE) .................... 10 2019 208 035.9

(51) Int. Cl.
*H01B 17/30*    (2006.01)
*H01B 1/02*    (2006.01)
*A61N 1/375*    (2006.01)

(52) U.S. Cl.
CPC ............. *H01B 17/305* (2013.01); *H01B 1/02* (2013.01); *A61N 1/3754* (2013.01)

(58) Field of Classification Search
CPC .................................................. H01B 17/305
USPC ....................................................... 174/667
See application file for complete search history.

(56) References Cited

U.S. PATENT DOCUMENTS

| | | | | | |
|---|---|---|---|---|---|
| 3,920,888 | A | * | 11/1975 | Barr | H01B 17/305 174/152 GM |
| 4,493,378 | A | * | 1/1985 | Kyle | H01B 17/305 174/152 GM |
| 5,175,067 | A | * | 12/1992 | Taylor | H01M 50/183 429/181 |
| 5,817,984 | A | * | 10/1998 | Taylor | A61N 1/3754 174/152 GM |
| 6,156,978 | A | * | 12/2000 | Peck | H01B 17/305 174/151 |
| 6,278,896 | B1 | | 8/2001 | Stehlik | |
| 9,741,463 | B2 | | 8/2017 | Leedecke | |
| 2002/0155350 | A1 | | 10/2002 | Spillman | |
| 2004/0101746 | A1 | | 5/2004 | Ota | |

(Continued)

FOREIGN PATENT DOCUMENTS

DE    19842943    3/2000

OTHER PUBLICATIONS ("Nickel-free austenitic stainless steels for medical applications", Institute of Metal Research, Feb. 26, 2010 (Year: 2010).*

(Continued)

*Primary Examiner* — Stanley Tso
(74) *Attorney, Agent, or Firm* — Ruggiero McAllister & McMahon LLC

(57) ABSTRACT

The disclosure relates to a glass-metal feedthrough, composed of an outer conductor or a basic body, a glass material or glass-ceramic material, and an inner conductor. The inner conductor is preferably a metal pin and the inner conductor is sealed in the outer conductor, in particular basic body, in the glass or glass-ceramic material. The metal pin comprises a material with high conductivity and/or low contact resistance, as well as a sleeve element that surrounds the metal pin at least partially.

15 Claims, 2 Drawing Sheets

(56) References Cited

U.S. PATENT DOCUMENTS

| | | | | |
|---|---|---|---|---|
| 2007/0187934 A1* | 8/2007 | Fink | ............... | F42B 3/103 |
| | | | | 280/737 |
| 2011/0031698 A1* | 2/2011 | Tziviskos | ............ | A61N 1/3754 |
| | | | | 277/312 |
| 2015/0090004 A1* | 4/2015 | Noel | ............... | G01N 3/24 |
| | | | | 73/37 |
| 2016/0001387 A1* | 1/2016 | Kronmueller | ........ | C25D 7/0614 |
| | | | | 228/101 |
| 2020/0121935 A1* | 4/2020 | Stevenson | ............ | A61N 1/3754 |

OTHER PUBLICATIONS

DIN EN1811, "Reference test method for release of nickel from all post assemblies which are inserted into pierced parts of the human body and articles intended to come into direct and prolonged contact with the skin", Oct. 2015, 31 pages.

DIN EN 12472, "Method for the simulation of wear and corrosion for the detection of nickel release from coated items (includes Amendment A1:2009) English version of DIN EN 12472:2009-09", Sep. 2009, 16 pages.

AISI 446.

* cited by examiner

GLASS-METAL FEEDTHROUGH HAVING A SLEEVE

CROSS-REFERENCE TO RELATED APPLICATION

The present application claims the benefit of German Patent Application No. 10 2019 208 035.9, filed on Jun. 3, 2019, which is herein incorporated by reference.

BACKGROUND OF THE DISCLOSURE

1. Field of the Disclosure

The disclosure relates to a glass-metal feedthrough, composed of an outer conductor or basic body, a glass material or glass-ceramic material, and an inner conductor in the form of a metal pin. The disclosure further relates to the use of a glass-metal feedthrough in a wearable item, in implantable medical devices and apparatuses, as well as elements having such a glass-metal feedthrough.

2. Description of the Related Art

Glass-metal feedthroughs are utilized in different fields of application of electrical engineering. For example, these are used for the feedthrough of electrical conductors in housings for components in electronics and sensor technology. In this context, components of this type have fused joints between glasses and various metal materials. Due to the sealing of an inner conductor made of metal into a glass or glass-ceramic material that is surrounded by an outer conductor made of metal, a hermetically tight feedthrough of a conductor into a housing can be provided. Very special glass-metal feedthroughs are those feedthroughs in which the feedthrough itself or parts of the feedthrough come into contact with the human body. In feedthroughs of this type, it happens that a high corrosion resistance as well as a good long-term stability of all components utilized are ensured. In particular, feedthroughs of this type should release only limited amounts of Ni in order to prevent the development of allergic reactions. This is defined in the Standards for the limit values of so-called nickel release. Concerning this, refer to German Industrial Standard (DIN) and European Standard (EN) 1811 and DIN/EN 12472.

Fe—Ni, Fe—Ni—Co, and Fe—Ni—Cr alloys are primarily utilized as materials for feedthrough conductors in the case of glass-metal feedthroughs. The advantage of these materials is their excellent adaptation to thermal expansion on sealing glasses. Of course, all these materials have significant percentages of Ni in the base material. Moreover, in order to protect the materials from corrosion, they have nickel coatings that in turn release nickel in undesired amounts.

In order to prevent a release of Ni, it has been provided in the prior art to coat the feedthrough conductor or inner conductor with a sufficiently thick gold layer, in order to reduce the nickel penetration. This had the disadvantage, of course, that it succeeded only insufficiently in preventing the release of Ni, or to achieve this prevention, very thick Au layers with a thickness of more than 2.5 µm were necessary.

Alternatively to a solution with coated conductors, DE 198 42 943 A1 proposes to use tantalum as the inner conductor or alternatively, nickel-free, stainless steel, and ferritic stainless steel. One example is the steel according to US Standard AISI 446, which involves a stainless, heat-stable, ferritic chromium steel with an aluminum addition.

The expansion coefficient of the ferritic stainless steel AISI 446 is only slightly higher than in common glasses. Therefore, there is the danger that the inner conductor contracts more strongly than the glass, and the interface to the glass cracks. In addition, the solderability of ferritic stainless steels is also limited and usually requires the use of a strong flux during soldering. This strong flux could lead to corrosion in later operation or would have to be extensively cleaned off prior to use.

Another disadvantage of DE 198 42 943 C2 is that the selection of Ni-free materials was limited, since a sufficient tightness of the feedthrough is only provided when the expansion coefficient of the inner conductor $\alpha_{inner}$ was less than the expansion coefficient of the glass $\alpha_{glass}$.

In order to provide a good conductivity, in the prior art, the metal pins were coated with nickel and/or gold. The problem resulted that Ni was released from such a configuration, at least unless the coating with gold was complete. On the other hand, metal pins made of pure copper or brass are glass-sealed only with great difficulty. Another problem of coated conductors is the corrosion that may occur in the presence of aqueous solutions or water. A material such as niobium and titanium that has an at least selective coating for a solder connection inside the housing, for example, by wet galvanic processes, is sufficient. These materials, however, can be galvanized adherently only with great difficulty. An improvement of solderability by preferred selective coating—e.g., by wet galvanic processes—is also technically difficult and therefore, expensive.

A feedthrough for batteries has been made known from US 2004/0101746 A1, in which the conductor is protected from the electrolyte by a covering.

U.S. Pat. No. 9,741,463 B2 shows a feedthrough for difficult environmental conditions in which the conductor together with a sleeve element that surrounds the conductor is sealed in a glass or glass-ceramic material.

A glass-metal feedthrough in which a sleeve element surrounds a conductor, and conductor and sleeve element are introduced together into a glass or glass-ceramic material has also become known from US 2002/0155350 A1.

SUMMARY OF THE DISCLOSURE

The object of the disclosure is thus to provide a glass-metal feedthrough that avoids the disadvantages of the prior art. In particular, a feedthrough with a metal pin or inner conductor shall be provided, which, on the one hand, does not release any nickel when it comes into contact with the human body, but on the other hand, also provides a sufficient solderability.

The above-stated object is achieved with a glass-metal feedthrough comprising an outer conductor, a glass material or glass-ceramic material, and an inner conductor. The inner conductor is a metal pin, and the inner conductor is sealed in the outer conductor, in the glass or glass-ceramic material. The metal pin comprises a material with high conductivity and/or low contact resistance, as well as a sleeve element that surrounds the metal pin at least partially. The metal pin has two ends, a first end and a second end, wherein the first end is sealed in the glass or glass-ceramic, and the second end receives the sleeve element.

The above-stated object of the disclosure is also achieved with use of the above-described feedthrough in a wearable item, in implantable medical devices or apparatuses. The above-stated object of the disclosure is also achieved with an element having the above-described feedthrough that can be introduced or attached to the human or animal body or to cell cultures containing living biological cells, wherein the outer conductor and the inner conductor are composed of materials that have a reduced allergenic potential, at least in their surface regions that come into contact with the human or animal body in the operating state.

The glass-metal feedthrough according to the disclosure is characterized in that it also comprises an outer conductor, which is also called a basic body, a glass material or glass ceramic, and an inner conductor that is preferably a metal pin and is sealed in the glass or glass-ceramic material. The inner conductor or metal pin is inserted in the outer conductor or basic body in the glass or glass-ceramic material and fused.

According to the disclosure, the material of the metal pin comprises a material with a high conductivity and/or a low contact resistance.

In addition, the metal pin or the inner conductor comprises a sleeve element that surrounds the circumference or perimeter of metal pin or inner conductor, at least partially, preferably completely. The sleeve element surrounds the metal pin only on a portion (e.g., at one end) of the metal pin and essentially serves for the purpose of providing the electrical contact of the metal pin, in the case of a lower resistance, to a conductor material, for example an opening in a printed circuit board, a so-called PCB (Printed Circuit Board). The sleeve material is the interface that is wetted by the soldering material during soldering.

It is particularly preferred that the sleeve element is not only put onto the metal pin and the pin is partially surrounded by the sleeve element, but also the sleeve element is pressed with the metal pin. It is ensured by the pressing that the sleeve element remains in the position provided on the metal pin and is not pulled away. During the pressing, the sleeve element is pressed with the metal pin by means of a pressing tool, pressing tongs or an electrical pressing machine. The sleeve element is solidly arranged on the metal pin by the pressing.

According to the disclosure, the metal pin of the glass-metal feedthrough has two ends, a first end that is sealed in the glass or glass ceramic material, and a second end that receives the sleeve, whereby the second end with the sleeve can be inserted or soldered into an electrical connection.

It is particularly preferred that the material of the sleeve comprises a solderable material, for example copper or nickel, since when it is inserted into the electrical connection, for example the opening of the printed circuit board (PCB), the sleeve then can be soldered to this electrical contact.

It is particularly preferred that the metal pin comprises a medically safe material, so that medical applications are possible. An electrically very conductive, medically safe material that also has a low contact resistance is, for example, niobium, titanium, tantalum, stainless steel, in particular a ferritic stainless steel, or molybdenum as the material for the metal pin.

If the metal pin is produced alone without a sleeve from these materials, e.g., niobium, titanium, tantalum or molybdenum, then in fact, a non-allergenic, electrically highly conductive material is used, which, however, can be only very poorly soldered to a conductor.

This problem is solved according to the disclosure in that a sleeve element of solderable material, for example copper, is pressed onto the metal pin made of niobium, titanium, tantalum, stainless steel, or molybdenum. The advantage of the materials niobium, titanium, tantalum, stainless steel, or molybdenum for the metal pin is not only the high conductivity, but also the fact that such materials thereof show practically no galvanic corrosion. The arrangement of a separate sleeve element or sleeve on the metal pin has the advantage that the well solderable materials thereof are not able to leak out and come into contact with humans. In addition to niobium, titanium, tantalum, stainless steel and molybdenum, suitable materials for the metal pin also include tungsten. The expansion coefficient of niobium amounts to approximately $7*10^{-6}1/K$, and that of molybdenum $5*10^{-6}1/K$.

The expansion coefficient of the metal pin $\alpha_{inner}$ lies preferably in the range of 4 to 13 ppm/K, i.e. from $4*10^{-6}1/K$ to $13*10^{-6} 1/K$. In contrast to the materials for the metal pin, the material of the sleeve, for example copper, has a higher expansion coefficient.

Based on the large differences in the thermal expansion coefficient during the sealing of the metal pin at temperatures of more than 600° C., it is expected that, based on the higher expansion coefficient, the sleeve composed of copper expands more intensely than the metal pin made of niobium or molybdenum, and the sleeve loses contact with the metal pin.

It has been surprisingly established that despite this fact, after a high temperature treatment, the copper sleeve is not stripped from the metal pin even with only slight pressing. This can be attributed to the fact that a diffusion bonding and thus a chemical compound of copper and metal pin is present, and not only a press connection. The usual temperatures of 800-1000° C. for producing a glass-metal connection are best suitable also for propelling the diffusion of the sleeve to the pin. The diffusion anchoring functions better, the higher the temperature is. In the present case, therefore, a separate process step for the diffusion anchoring of the sleeve is not necessary. The diffusion proceeds in parallel to the glass-sealing process.

Based on the sealing of the metal pin, it is particularly preferred that the thickness of the feedthrough is smaller than 1 mm. This is achieved, in particular, with a basic body made of metal, ceramic, and/or glass.

If the connection between contact pin and a basic body is produced by means of a polymer, e.g., by overmolding, at least 2 mm is required in order to obtain, e.g., a water-pressure stability of 5 bars. Thinner glass-metal feedthroughs made of metal thus essentially lay claim to less space, which is why metal is preferred as the material for the basic body.

The use of niobium, titanium, tantalum, and molybdenum as the material for the metal pin has the advantage that soldering materials do not move up due to wetting, but are limited only to the region of the sleeve element or sleeve. The limiting of the soldering material to the sleeve region has the additional advantage that the soldering process can be better controlled than in the case of forming the entire metal pin of copper, for example.

The glass-metal feedthrough according to the disclosure above all is used in wearable items, in implantable medical devices or apparatuses, wherein both the outer conductor and the inner conductor come into contact with the human or animal body, at least in surface regions in the operating state.

The configuration of the metal pin according to the disclosure possesses a reduced allergenic potential, in particular since no nickel or chromium is released from the metal pin. In addition to the named materials, stainless steel, in particular a ferritic stainless steel, can also be used for the metal pin.

It is particularly preferred if the outer conductor or basic body of the glass-metal feedthrough is an austenitic stainless steel, preferably the stainless steel 316 L, which is characterized by a good weldability and a high expansion coefficient.

The metal pin made of niobium or molybdenum has an expansion coefficient $\alpha_{inner}$ in the range of $5*10^{-6}$1/K to $7*10^{-6}$1/K, which is smaller than that of the glass material, so that a tight feedthrough, in particular a hermetically tight feedthrough is provided. In addition to molybdenum and niobium for the inner conductor, tungsten, stainless steel, or tantalum can be used. Preferably, the expansion coefficients of the outer conductor or basic body are selected so that a joint pressure on the inner conductor or metal pin of at least 30 MPa, preferably at least 50 MPa, in particular at least 100 MPa is provided.

In such a case, a compression sealing is involved. The disclosure can also be used, however, in adapted feedthroughs. In such a case, not only a glass sealing in metal material is possible, but also a sealing in a ceramic body. Sealings in ceramics can be conducted on glass only under certain conditions with pressure preloading.

The disclosure additionally comprises the use of the glass-metal feedthrough according to the disclosure in implantable medical devices or apparatuses as well as providing an element having a glass-metal feedthrough according to the disclosure that can be introduced into or attached to a human or animal body or to cell cultures containing living biological cells, wherein the outer conductor and the inner conductor are composed of materials, particularly metals, that have a reduced allergenic potential, at least in their surface regions that are in contact with the human or animal body in the operating state.

The material of the outer conductor or basic body and of the inner conductor or metal pin can come into contact with the human or animal body or cell cultures and is preferably characterized in that it does not release any nickel and/or chromium.

Preferably, the material of the outer conductor comprises nickel-free and/or chromium-free stainless steel and/or austenitic stainless steel and/or a ceramic and/or a glass ceramic, at least in its surface regions that come into contact with the human or animal body or biological cells of the cell culture in the operating state. Materials that fulfill the requirement of nickel release testing according to DIN EN1811 and DIN EN12472 are particularly preferred.

Preferably, the material of the inner conductor comprises nickel-free and/or chromium-free stainless steel and/or niobium and/or titanium and/or tantalum and/or tungsten, at least in its surface regions that come into contact with the human or animal body or biological cells of the cell culture in the operating state. Materials that fulfill the requirement of nickel release testing according to DIN EN1811 and DIN EN12472 are particularly preferred.

The disclosure will be described extensively once more below on the basis of the figures.

DETAILED DESCRIPTION OF THE DISCLOSURE

Figure 1:
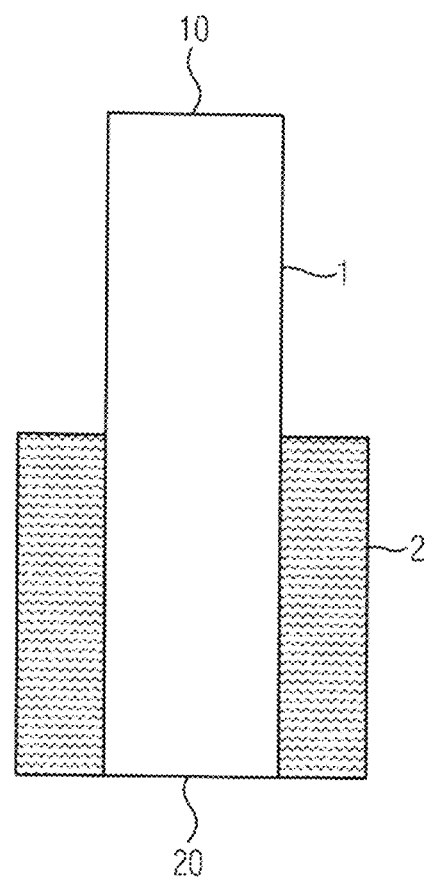
FIG. 1 a schematic, cross-sectional representation of a metal pin having a sleeve element according to the disclosure.

FIG. 1 shows a schematic cross-sectional representation of a metal pin 1 having a sleeve element 2 according to the disclosure. The metal pin 1 comprises a material having a high electrical conductivity and biocompatibility, for example niobium, titanium, tantalum, molybdenum, stainless steel, or tungsten. In the shown embodiment, metal pin 1 is round, and sleeve element 2 is sleeve- or ring-shaped. As described above, sleeve element 2 surrounds the circumference of metal pin 1, at least partially, or completely.

The metal pin 1 has two ends, a first end 10 and a second end 20. In a glass-metal feedthrough, the first end 10 of the metal pin 1 is usually sealed in a glass or glass-ceramic material. According to the disclosure, the sleeve element 2 or the sleeve is attached on the second end 20 of the metal pin 1, preferably by pressing, whereby a fusion of the metal of the sleeve element 2 with the metal pin 1 can also take place during the heating. Any material that is well solderable, for example, to electrical contacts is possible for the sleeve element 2. Well solderable materials can include copper, nickel, etc. When sleeve element 2 is pressed to metal pin 1, the pressing should be such that sleeve element 2 retains its ring or round shape. The fusion between the material of sleeve element 2 and metal pin 1 can happen for several different types of materials used in each. That is, as described earlier in this present disclosure with respect to copper, diffusion bonding and thus a chemical compound comprising materials from sleeve element 2 and metal pin 1 can be created by the pressing of sleeve element 2 to metal pin 1.

Figure 2:
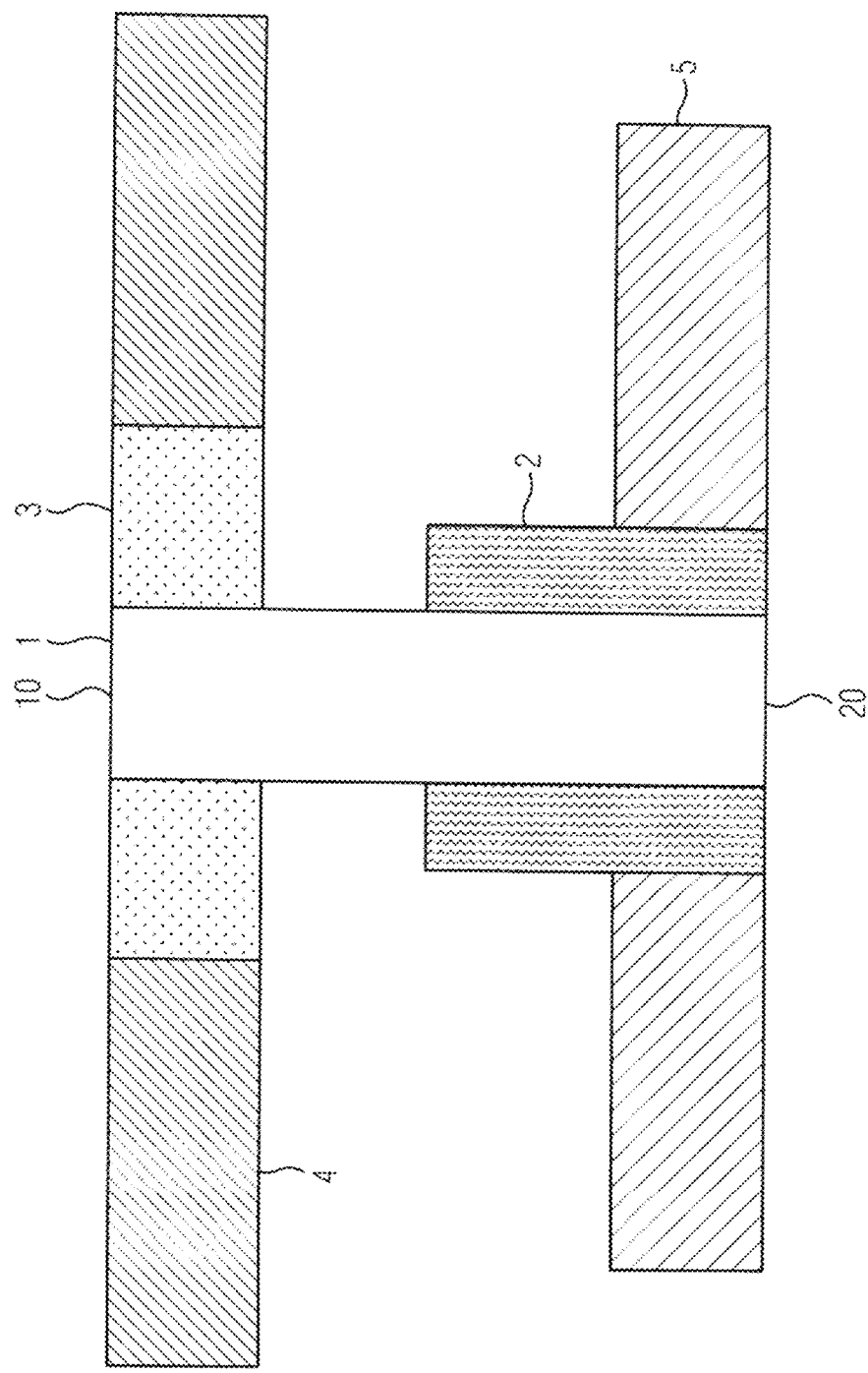
FIG. 2 a schematic representation of a metal pin having a sleeve element according to the disclosure in a feedthrough.

The use of a metal pin 1 according to the disclosure as shown in FIG. 1 is depicted in a glass-metal feedthrough in FIG. 2, in which the metal pin 1 according to the disclosure is connected to an electrical contact, a printed circuit board (PCB) 5 in the exemplary embodiment shown. The first end 10 of the metal pin 1 is sealed according to the disclosure in a glass or glass-ceramic material 3 resulting in a glass-metal feedthrough. The glass material 3 is surrounded by an outer conductor or a basic body 4. The material for the basic body 4 can be a metal, for example, in particular stainless steel, but also a ceramic. With the use of a metal, due to different expansion coefficients of the metal of the basic body 4 and the glass material 3, a compression sealing is present. Adapted feedthroughs would also be possible, for example with the use of a ceramic material for the basic body 4. In the shown embodiment, glass material 3 is in a ring-shape that surrounds metal pin 1.

The thickness of the basic body 4 having a sealed metal pin 1 usually lies in the range of less than 1 mm. The sleeve 2 surrounds the metal pin 1 at the unsealed second end 20 and is presently inserted in an opening of a conductor material, here the printed circuit board (PCB) 5. The first end 10 of the metal pin 1 is introduced in the glass or glass-ceramic material 3.

A metal pin 1 that is characterized by a high biocompatibility, a high electrical conductivity, a very good solderability, and a high resistance to corrosion is provided for the first time by the disclosure.

The present disclosure comprises aspects that are set forth in the following clauses, which are part of the description, but are not claims.

Clauses a. A glass-metal feedthrough, composed of an outer conductor or a basic body (4), a glass material or glass-ceramic material, and an inner conductor, wherein the inner conductor is preferably a metal pin, and the inner conductor is sealed in the outer conductor, in particular basic body (4), in the glass or glass-ceramic material, is hereby characterized in that the metal pin comprises a material with high conductivity and/or low contact resistance, as well as a sleeve element that surrounds the metal pin at least partially.

b. The glass-metal feedthrough according to clause a, further characterized in that the sleeve element is pressed with the metal pin.

c. The glass-metal feedthrough according to clause a or b, further characterized in that the material of the sleeve element comprises a solderable material, in particular copper or nickel.

d. The glass-metal feedthrough according to one of clauses a to c, further characterized in that the metal pin comprises a medically safe material, in particular one of the following materials: niobium, molybdenum, titanium, tantalum, stainless steel, and tungsten.

e. The glass-metal feedthrough according to one of clauses a to d, further characterized in that the metal pin has two ends, a first end (10) and a second end, wherein the first end is sealed in the glass or glass-ceramic, and the second end receives the sleeve element.

f. The glass-metal feedthrough according to one of clauses a to e, further characterized in that the expansion coefficient of the metal pin $\alpha_{inner}$ lies in the range of 4 to 13 ppm/K.

g. Use of the glass-metal feedthrough according to one of clauses a to fin a wearable item, in implantable medical devices or apparatuses.

h. An element having a glass-metal feedthrough according to one of clauses a to f that can be introduced or attached to the human or animal body or to cell cultures containing living biological cells, wherein the outer conductor and the inner conductor are composed of materials, in particular metals that have a reduced allergenic potential, at least in their surface regions that come into contact with the human or animal body in the operating state.

i. The element according to clause h, wherein the material of the outer conductor and of the inner conductor in contact with the human or animal body or the cell cultures does not release any nickel and/or chromium.

j. The element according to at least one of clauses g or h, wherein the material of the outer conductor and of the inner conductor comprises nickel-free and/or chromium-free stainless steel and/or austenitic stainless steel and/or a ceramic and/or a glass and/or a glass ceramic, at least in their surface regions that come into contact with the human or animal body or biological cells of cell culture in the operating state.

k. A glass-metal feedthrough, comprising: an outer conductor, a material comprising glass or glass-ceramic, an inner conductor, wherein the inner conductor is a metal pin, and the inner conductor is sealed in the material, and the material is surrounded by the outer conductor; and a sleeve element that surrounds the metal pin at least partially. The metal pin comprises a material with high conductivity and/or low contact resistance. The metal pin has two ends, a first end and a second end, wherein the first end is sealed in the material, and the sleeve element surrounds the metal pin at least partially at the second end.

What is claimed is:

1. A glass-metal feedthrough, comprising:
   an outer conductor;
   a material comprising glass or glass-ceramic;
   an inner conductor, wherein the inner conductor is a metal pin having a first end and a second end, wherein the first end is sealed in the material, and the material is surrounded by the outer conductor; and
   a sleeve element is placed on the metal pin and is in direct contact with the metal pin, wherein the sleeve element surrounds the second end at least partially,
   wherein the sleeve element comprises a second material that comprises solderable copper or nickel.

2. The glass-metal feedthrough according to claim 1, wherein the metal pin comprises a second material that is medically safe, and is selected from the group consisting of niobium, molybdenum, titanium, tantalum, stainless steel, and tungsten, and combinations thereof.

3. The glass-metal feedthrough according to claim 2, wherein the metal pin comprises a third material that is medically safe, and is selected from the group consisting of niobium, molybdenum, titanium, tantalum, stainless steel, and tungsten, and combinations thereof.

4. The glass-metal feedthrough according to claim 3, wherein the expansion coefficient of the metal pin $\alpha_{inner}$ is in the range of 4 to 13 ppm/K.

5. The glass-metal feedthrough according to claim 1, wherein the expansion coefficient of the metal pin $\alpha_{inner}$ is in the range of 4 to 13 ppm/K.

6. A wearable, implantable medical device comprising the glass-metal feedthrough according to claim 1.

7. An element comprising the glass-metal feedthrough according to claim 1, wherein the element can be introduced or attached to the human body, an animal body, or to cell cultures containing living biological cells, wherein the outer conductor and the inner conductor are composed of materials that are medically safe, at least in their surface regions that come into contact with the human body, animal body, or cell cultures containing living biological cells.

8. The element according to claim 7, wherein the material of the outer conductor and of the inner conductor in contact with the human or animal body or cell cultures does not release any nickel and/or chromium.

9. The element according to claim 7, wherein the materials of each of the outer conductor and of the inner conductor comprise a material selected from the group consisting of nickel-free and/or chromium-free stainless steel, austenitic stainless steel, a ceramic, a glass, a glass ceramic, and any combinations thereof, at least in their surface regions that come into contact with the human or animal body or biological cells of cell culture in the operating state.

10. The glass-metal feedthrough according to claim 1, wherein the sleeve element does not extend beyond the metal pin.

11. The glass-metal feedthrough according to claim 1, wherein the sleeve element is not sealed in the material.

12. The glass-metal feedthrough according to claim 1, further comprising a printed circuit board having an opening, wherein the sleeve element that at least partially surrounds the metal pin is within the opening of the printed circuit board.

13. The glass-metal feedthrough according to claim 12, wherein the opening of the printed circuit board is an electrical contact and the sleeve element is soldered to this electrical contact.

14. The glass-metal feedthrough according to claim 1, wherein the sleeve element is diffusion bonded to the metal pin.

15. A glass-metal feedthrough, comprising:
   an outer conductor;
   a material comprising glass or glass-ceramic;
   an inner conductor, wherein the inner conductor is a metal pin having a first end and a second end, wherein the first end is sealed in the material, and the material is surrounded by the outer conductor; and a sleeve element that surrounds the second end at least partially, wherein the sleeve element comprises a second material that comprises copper or nickel, and wherein the sleeve element is pressed to and is in direct contact with the metal pin.

\* \* \* \* \*